United States Patent [19]

Wenz

[11] Patent Number: 5,440,393
[45] Date of Patent: Aug. 8, 1995

[54] PROCESS AND DEVICE FOR MEASURING THE DIMENSIONS OF A SPACE, IN PARTICULAR A BUCCAL CAVITY

[75] Inventor: Heinz V. Wenz, Hanau, Germany
[73] Assignee: Com Dent GmbH, Berlin, Germany
[21] Appl. No.: 952,859
[22] PCT Filed: Mar. 13, 1990
[86] PCT No.: PCT/EP90/00404
§ 371 Date: Nov. 13, 1992
§ 102(e) Date: Nov. 13, 1992
[87] PCT Pub. No.: WO91/13585
PCT Pub. Date: Sep. 19, 1991
[51] Int. Cl.⁶ .................. A61B 5/103; G01B 11/24
[52] U.S. Cl. .................... 356/376; 128/777; 35.4/62; 348/66
[58] Field of Search ............ 356/376; 354/62; 433/25, 213, 215, 229; 128/777; 348/66

[56] References Cited

U.S. PATENT DOCUMENTS

| | | |
|---|---|---|
| 3,382,781 | 5/1968 | Hamilton . |
| 4,070,683 | 1/1978 | Altschuler et al. ............ 356/2 |
| 4,453,082 | 6/1984 | Pryor . |
| 4,525,858 | 6/1985 | Cline et al. . |
| 4,575,805 | 3/1986 | Moermann et al. .......... 356/376 |
| 4,611,288 | 9/1986 | Duret et al. .................. 356/376 |
| 4,724,525 | 2/1988 | Purcell et al. . |
| 4,742,464 | 5/1988 | Duret et al. .................. 364/474 |
| 4,952,149 | 8/1990 | Duret et al. .................. 356/376 |
| 4,964,770 | 10/1990 | Steinbichler et al. ........ 356/376 |

FOREIGN PATENT DOCUMENTS

| | | |
|---|---|---|
| 2022083 | 3/1971 | Germany . |
| 2412763 | 10/1974 | Germany . |
| 3810455 | 10/1989 | Germany . |
| 3817561 | 11/1989 | Germany . |
| 2155628 | 9/1985 | United Kingdom . |
| 8603292 | 6/1986 | WIPO ........................ 356/402 |

Primary Examiner—Richard A. Rosenberger
Attorney, Agent, or Firm—Wenderoth, Lind & Ponack

[57] ABSTRACT

A process for measuring the dimensions of the buccal cavity with upper and lower jaw dentition uses a scanning device that is at least partially introduced into the buccal cavity. The scanning device is an optical measurement device whose optical signals are converted into electronic signals, which electronic signals can then be evaluated by a computer. A source of optical radiation is located in a preferably extra-oral section of the device, and a projection device with a projection optical system projects optical radiation onto the surfaces and/or the translucent internal volume of the buccal cavity and the colored translucent volume of the teeth. A recording device having a recording optical system records the radiation reflected from the surfaces and/or the translucent internal volume, and an evaluation device preferably located in an extra-oral section of the device evaluates the recorded reflected radiation.

30 Claims, 6 Drawing Sheets

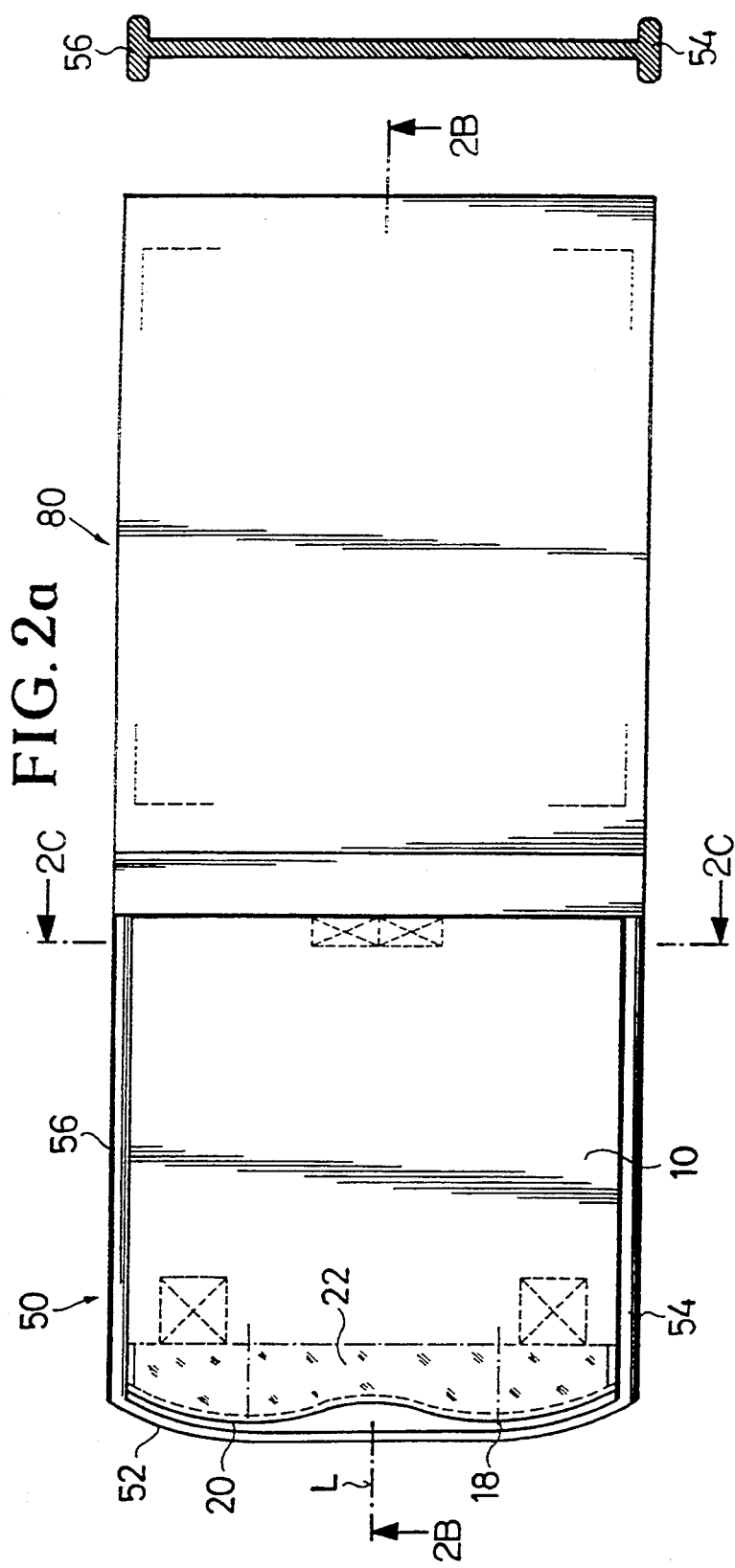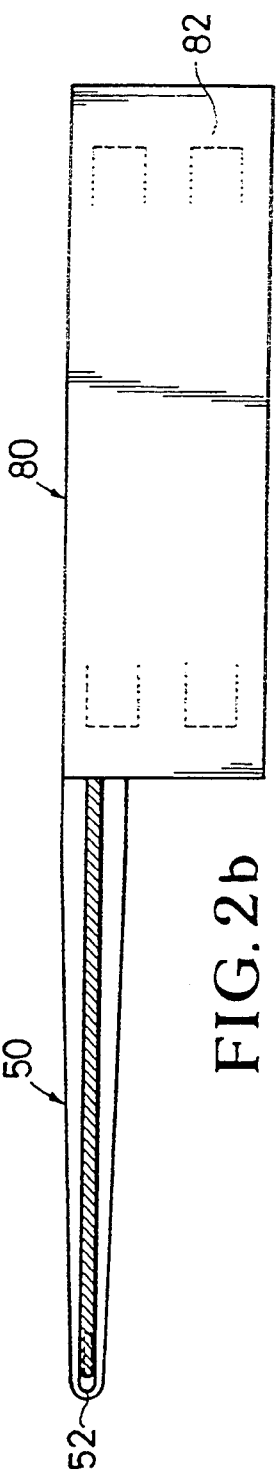

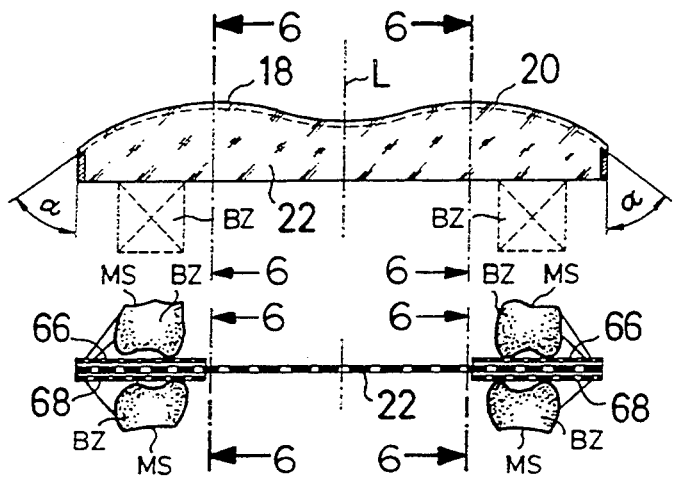
FIG.5a
FIG.5b
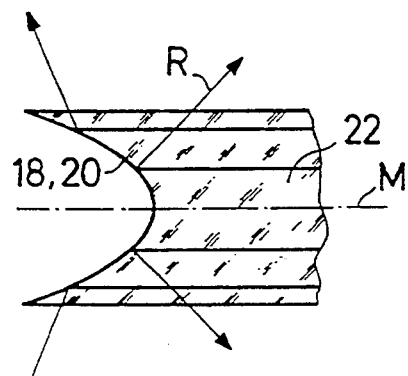
FIG.6a
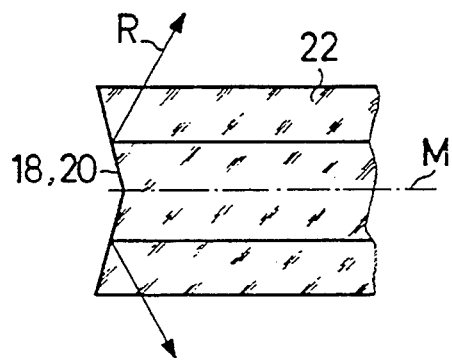
FIG.6b
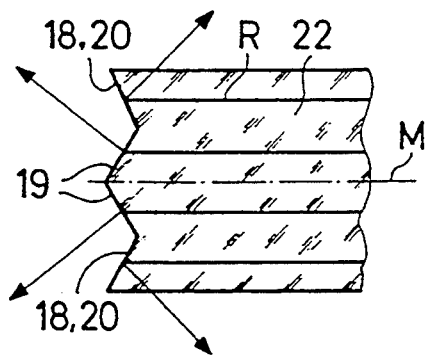
FIG.6c
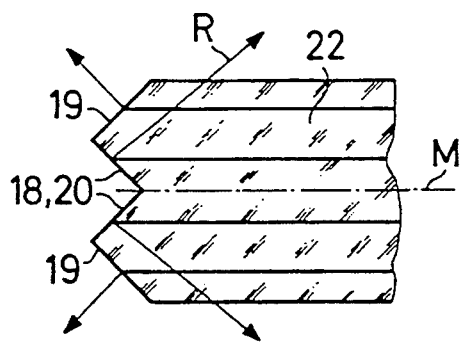
FIG.6d

PROCESS AND DEVICE FOR MEASURING THE DIMENSIONS OF A SPACE, IN PARTICULAR A BUCCAL CAVITY

BACKGROUND OF THE INVENTION

1. Field of the Invention

The present invention relates to a process for measuring the dimensions of a space, in particular a buccal cavity with upper and lower jaw dentition, using a scanning device that is introduced at least in part into the space that is to be measured, and a device for carrying out this process.

2. State of the Prior Art

Processes used to measure upper and lower dentition and apparatuses for carrying out such processes are known, for example, in the form of the dental use of mechanical impression trays. When this is done, a pair of impression trays an upper jaw impression tray and a lower jaw impression tray) that correspond to the anatomical conditions of the buccal cavity of the particular patient are selected and are checked with respect to size and fit by inserting them into the buccal cavity. After the selection and checking of a suitable pair of impression trays, both of the impression trays are filled with a paste-like impression paste and are then inserted into the patient's buccal cavity in such a way that the impression paste of one impression tray surrounds the upper jaw dentition evenly and the impression paste in the other impression tray surrounds the lower jaw dentition in the same way. The impression paste solidifies within a few minutes, and when the paste is still in the elastic state it, together with the particular impression tray, is released from the upper or lower jaw dentition, respectively, and removed from the patient's mouth. Once the impression paste has finally hardened, this is inserted into a suitable outer tray and the tray is then filled with plaster of Paris or a similar substance. As soon as this plaster of Paris, or a material that is like it, has hardened, the impression paste is removed. In this way, one obtains a geometric-topographic impression of the configuration of the buccal cavity, in particular in the area of the dentition, such as may be required, for example, for orthopaedic work that is to be done on the jaw or else for the production of dental protheses or the like. A disadvantage in this known process and device is the inconvenient and time-consuming production of an impression, the lack of any correlation between the upper and lower jaw impressions, the lack of any measurement of the articulation of the jaw, the inaccuracy of the process that is brought about by many possibilities for error and the difficulties involved in evaluating the results that are obtained.

SUMMARY OF THE INVENTION

It is the task of the present invention to improve a process of the type described in the introduction hereto in order to be able to obtain exact and, as far as possible, error-free measured values, in particular with reference to the configuration of the upper and lower dentition, and to do this by simple manipulation and in a short period of time, the result being a signal that is amenable to further processing. In addition, the present invention proposes a scanning device with which this process can be carried out using simple mechanical means. Essentially, this problem has been solved according to the present invention in that an optical measurement system is used as a scanning device, the optical signals of which can be converted into electronic signals that can be evaluated by means of a computer.

In this way, the buccal cavity can be measured precisely without using an impression paste and the measured data evaluated by computer, so that extremely valuable measurement results are made available in a very short period of time.

In one advantageous configuration of the process according to the present invention, optical radiation is projected onto portions of the buccal cavity, i.e. the surfaces and/or the translucent internal volume of the buccal cavity that is to be measured, in particular the translucent teeth, by means of a projection system, and the radiation that is reflected from the surfaces and/or the translucent internal volume is recorded by means of a recording system, by means of which the geometric-topographical configuration of the buccal cavity can be recorded without contact with any part of the buccal cavity.

A particularly high level of precision can be achieved by using a fine pattern, for example, a strip pattern that is generated by interference.

In a development of the present invention, the reflected radiation is recorded with a stereo-photogrammetric recording system or one that works by the triangulation principle or according to the principle of a hologram, this making it possible to carry out extremely precise three-dimensional geometric-topographic measurement.

The value of the measurements can be significantly increased even more if, as with a particular configuration of the present invention, the projected and/or the reflected radiation is projected onto the surface of the buccal cavity that is to be measured and/or recorded from the surfaces of the buccal cavity line by line, as a result of relative movement of the projection system and/or of the recording system, in particular in the longitudinal direction, relative to the buccal cavity. By generating intermediate images of the moving upper jaw dentition, it is possible to draw accurate conclusions concerning the articulation movement of the jaw.

In a further particularly advantageous configuration of the present invention, instead of being formed on a line sensor, optionally by means of folding optics, the optical signals are formed on a plane sensor, where they can be converted into electronic signals that can be easily processed.

The electronic signals can be processed to form images and displayed on a screen, which facilitates evaluation of data that has been obtained.

In addition to the foregoing, the processed electronic signals can also be passed directly to a computer-controlled production system that is used to produce replacement parts for teeth, so that fully automatic production is made possible.

A further development of the present invention makes provision for the fact that the optical measurement device can be used for working directly on the buccal cavity by increasing the power supplied to it when, in the first instance, the use of a laser, in particular a YAG-argon laser with low penetration, is used for cryosurgical work, or an argon-fluoride excimer laser is used for working on ceramic or hard substance (enamel) of the teeth, without any thermal secondary effects, using photoablation.

The present invention also relates to a scanning device for carrying out the process described heretofore, which is characterized by a source of optical radiation that is preferably located in an extra-oral section of the device and a projection device with a projection optical system, a recording device with a recording optical system and an evaluation device, located preferably in an extra-oral section of the device with which the buccal cavity can be measured precisely and which supplies rapid, easily evaluated and verifiable results.

In a further development of the device according to the present invention, the projection device projects a defined optical radiation pattern onto the surfaces and-/or the translucent internal volume of the buccal cavity, in particular of the translucent teeth, which then forms the basis for the geometric-topographic mapping of the buccal cavity by means of triangulation.

In order to ensure particularly simple evaluation of the projected radiation, in another advantageous configuration the optical pattern that is generated by the projection device is a strip pattern.

As in another advantageous configuration of the present invention, a precisely defined strip pattern can be generated using an interferometer. As an example, a Michelson interferometer is particularly suitable. In order to provide for particularly fine and exact adjustment of the strip interval, the mirror of the interferometer can be adjusted by means of a piezo-electric device.

In another configuration of the present invention, the projection device incorporates a light source that preferably radiates light that resembles sunlight, by means of which the colour of the teeth can be determined. Because of the fact that the teeth are translucent and because light of different wavelengths penetrates the teeth to different depths from where it is reflected at different strengths, three-dimensional measurement of the coordinates of the color locations is indispensable for precise color recognition, i.e., for the exact mapping of the pigment arrangement in a three-dimensional translucent cavity. Ultraviolet light with a wavelength of 300 nm can be used to carry out a fluorescence test, whereas a metameric test is best effected with tungsten light (1500 lux, attenuated).

A laser is particularly suitable as a source of radiation, the laser radiating either monochromatic light of a specific wavelength, as in the case, for example, of a helium-neon laser, or which is so designed as to be of variable frequency, i.e., adjustable to different wavelengths, such as, for example, an alexandrite laser, in which the radiated light is preferably polarized, i.e., only oscillates in a single plane of oscillation in order to generate a sharp and easily evaluated strip pattern. It is, of course, understood that, in addition to the laser, an additional source of light can be provided, which similarly serves to determine the color of the teeth. Instead of a laser that generates coherent light, it is also possible to incorporate a monochromator. A laser can also be used to generate a hologram.

In order to achieve even illumination of the buccal cavity, another configuration of the present invention provides for the fact that the projection device incorporates a system of illuminating optics. Even illumination of the buccal cavity is advantageous for achieving a high degree of resolution. The optical illuminating system can also have an associated polarizer, preferably a circular polarizer that is electronically adjustable, since polarized light is required for specific applications such as, for example, optical measurement of forces.

In a further advantageous configuration of the present invention, even illumination of the upper and lower dentition is achieved by using a deflection system that can deflect the projection radiation within the buccal cavity in an appropriate manner, for example, in order to reach the front and rear surfaces as well as the marginal spaces or crown edges, respectively, of the teeth.

In order to ensure good recording quality, the recording device can also incorporate a deflection system, so that, for example, the radiation reflected from the rear surfaces of the teeth can also be recorded.

A simple and reliable type of deflection is achieved in an advantageous development of the present invention in that the deflection system incorporates a mirror or system of mirrors.

An improvement of the deflection system can be achieved by using a double or multiple mirror or similar suitable deflection elements. The mirror can also be sinusoidal in order to achieve a continuous panoramic effect.

Particularly even imaging is ensured if the mirror or mirror system is configured so as to be aspherical.

In a further development of the invention, the deflection system incorporates a glass body that is mirrored in order to ensure a high level of stability and, simultaneously, low thermal expansion of the mirror or mirror system, respectively, for a given and small installed depth. In order to be able to exploit the optical refraction of the glass body in sub-areas, it may be only partially mirrored. If the mirrored surface of the glass body is only semi-transparent, this can be used for holographic measurement. It is particularly advantageous if the mirroring is applied to the edge of the glass body that is remote from the source of light, because the mirroring can be inserted deep into the oral cavity in this way if the deflection device is particularly shallow.

In a further advantageous configuration of the present invention the mirror or the mirror system and/or the glass body are/is arranged on a mirror carrier, which permits particularly smooth guidance of the mirror or glass body, respectively.

The mirror carrier can be moved along a guide relative to the buccal cavity in order to permit illumination or recording of the buccal cavity from various positions.

In a further configuration of the present invention the mirror carrier can be moved in the direction of the longitudinal axis of the projection device, in particular of the optical illuminating system, or of the recording device, respectively, and in particular of the optical recording system, and preferably together with the optical illuminating system and the optical recording system, continuously or incrementally, this permitting linear scanning of the buccal cavity with a particularly high level of resolution and constant depth of focus. A linear DC motor with an integrated position sensor is particularly well suited as a drive system for doing this.

The recording device and, under certain circumstances, the projection device, can be adjustable relative to the mirror carrier, perpendicular to the horizontal mid-plane of the mirror or glass body, respectively, so that the angle of reflection of the mirror can be varied in order to effect a further improvement of the panoramic effect between the front and rear surfaces of the teeth.

In order to protect the deflection device from outside influences, and in order to provide for simple disinfection after use, and at the same time, however, to ensure that it functions properly, an advantageous development of the present invention provides that the deflection device is arranged in a housing that is, at least in part, transparent. In addition, the housing or the mirror carrier can be mirrored so as to be semi-transparent on either the inside or the outside in order to permit the production of holograms.

More advantageously, this housing can incorporate an inserted layer or an applied layer of polycarbonate or a similar material that is suitable for optical stress measurement, so that if polarized light is used and the polycarbonate surface is mirrored, the device can be used for measuring forces by way of isochromatic evaluation in the reflected polarized light.

In a further configuration of the present invention, in order to reduce patient stress as far as possible, the housing of the deflection system is essentially matched to the anatomical volume relationships of the buccal cavity.

A flat configuration of the housing is particularly advantageous in order that it can be inserted easily between the upper and lower dentition and carry out extrapolations of the movement function within the rotative range of movement of the mandibular joint in order to find the terminal axis of rotation. In the case of the force measurement, for which provision is also made, a flat configuration of the housing is similarly advantageous, for the forces of the teeth that are biting down can be measured when the dentition is almost closed.

In a further advantageous configuration of the present invention, the deflection device of the projection device is also configured as the deflection device for the recording device, which permits a particularly simple and compact construction and reduces the number of possible sources of error.

In another version of the present invention, a further reduction of the number of the possible effects of errors is achieved in that the deflection device, the drive unit for the deflection device, and the optical recording system are arranged in a common housing.

In the same way, it is also an advantage that the projection device, in particular the optical illuminating system, the deflection device, and the recording device, in particular the optical recording system, be configured as a moveable unit in order to preclude errors, in particular changes in the depth of focus, caused by undesired relative movement,.

In a further advantageous configuration, a trigger device that is preferably controlled by the position of the mirror carrier, is incorporated. Using the trigger device, for example, the firing sequence of; the laser lamp can be so triggered that sharp images result during the movement of the deflection device. In this way, it is possible to avoid blurring caused by movement. When this is done, the triggering frequency can be on the order of magnitude of approximately 10,000 Hz so that a recording time of one second can be achieved at a resolution of 10,000 lines.

A further, and particularly advantageous, configuration of the present invention incorporates a digitizing device that converts the optical signals from the recording device into electronic signals. This digitizing device reveals the principle advantages of the invention in that it permits rapid, comprehensive, and precise processing and evaluation of the signals that are obtained.

In addition to a line sensor, a conventional video camera with a plane sensor can be used as a digitizing device; this is comparatively cost-effective and provides sufficient resolution.

In order to be able to take advantage of all the possibilities of such a plane sensor, it is expedient, as in another configuration of the present invention, to incorporate a folded optical system between the recording device and the digitizing device in order to convert the optical line pattern of the recording device into an area pattern.

The optical signals from the device can then be more simply interpreted if the position of the mirror carrier of the deflection device is also mapped at each point in time. To this end, in a further configuration of the present invention, the digitizing device incorporates a sensor to determine the position of the mirror carrier. Then the light source can be triggered expediently and in the same way by the digitizing device.

In the same way, in certain cases, such as, for example, during three-dimensional color measurement, the wavelength of the light that is radiated and received is important for evaluating the optical signals. For this reason, a further configuration of the present invention incorporates a digitizing device with a sensor that is used to determine the wavelength of the light that is radiated and of the light that is received and which has been transformed and reflected by the object, which is important if a variable-frequency monochromator or laser, e.g., an alexandrite laser, is used. In place of this, a red-green-blue color sensor that provides for white balance can also be used.

In a further configuration of the present invention, the digitizing device is also provided with a sensor for preferably indirect determination and possibly for adjustment of the strip interval or the strip width of the strip the strip pattern, for both are important for evaluating the optical signals by means of triangulation.

In an advantageous development of the invention the projection device can also be used for working on the buccal cavity, by increasing the radiation energy, and in particular for working on the teeth by means of a laser. In this way, the projection device can also be used as a working instrument.

In order to be able to make valid statements about tooth movement and tooth forces under the action of force in addition to determining the geometric-topographic configuration of the buccal cavity and three-dimensional color recognition of the translucent teeth, in a further advantageous configuration of the present invention the intra-oral section of the device is configured as a force-measurement device.

If a pyro-electric detector such as a foil is used, the force-measurement device can be kept particularly flat so that the measurement of forces can be effected with the dentition almost closed.

In order to be able to measure the forces simultaneously in different directions, in a particularly advantageous configuration of the present invention, the pyro-electric detector incorporates biaxially oriented layers of pyro-electric material.

In a particularly advantageous configuration of the present invention the force-measurement device is provided with an isochromatic evaluation device which, in addition to a source of polarized light or a polarizer, incorporates an inserted layer of polycarbonate or similar material in the housing of the deflection device, in addition to a mirrored surface and an analyzer that is preferably associated with the optical recording system.

BRIEF DESCRIPTION OF THE DRAWINGS

Further objects, advantages, and possible applications of the present invention are set out in the following description of embodiments that are described on the basis of the drawings. All of the features that are described and/or illustrated constitute either singly, or in any meaningful combination, the object of the present invention. These drawings show the following:

FIG. 2a: a plan view of a measurement device according to the present invention, consisting of a deflection device, an optical illuminating system, an optical recording system, and a drive unit for the deflection device, arranged in a device housing;

FIG. 2b: a cross section through the measurement device of FIG. 2a taken along line 2b—2b;

FIG. 2c: a cross section of an intra-oral section of the measurement device of FIG. 2a, taken the line 2c—2c;

FIG. 3a: a vertical cross section through the intra-oral section of the measurement device taken along line 3a—3a of.

FIG. 3b: a horizontal cross section through the intra-oral section of the measurement device taken along line 3b—3b of; FIG. 3a;

FIG. 5a: a plan view of a glass body of the deflection device that is provided with an aspherical sinusoidal mirror;

FIG. 5b: a diagram showing the arrangement of the intra-oral section of the measurement device between the teeth of the upper and lower jaw;

FIG. 6a: a vertical cross section through the glass body of the deflection device taken, on lines 6—6 in FIGS. 5a and 5b;

FIG. 6b: a vertical cross section through a further embodiment of a glass body of the deflection device taken on lines 6—6 in FIGS. 5a and 5b;

FIG. 6c: a vertical cross section through yet another embodiment of a glass body of the deflection device taken, along lines 6—6 of in FIGS. 5a and 5b;

FIG. 6d: a vertical cross section through yet another embodiment of a glass body of the deflection device taken along lines 6—6 of FIGS. 5a and 5b;

DETAILED DESCRIPTION OF THE PREFERRED EMBODIMENT

Figure 1:
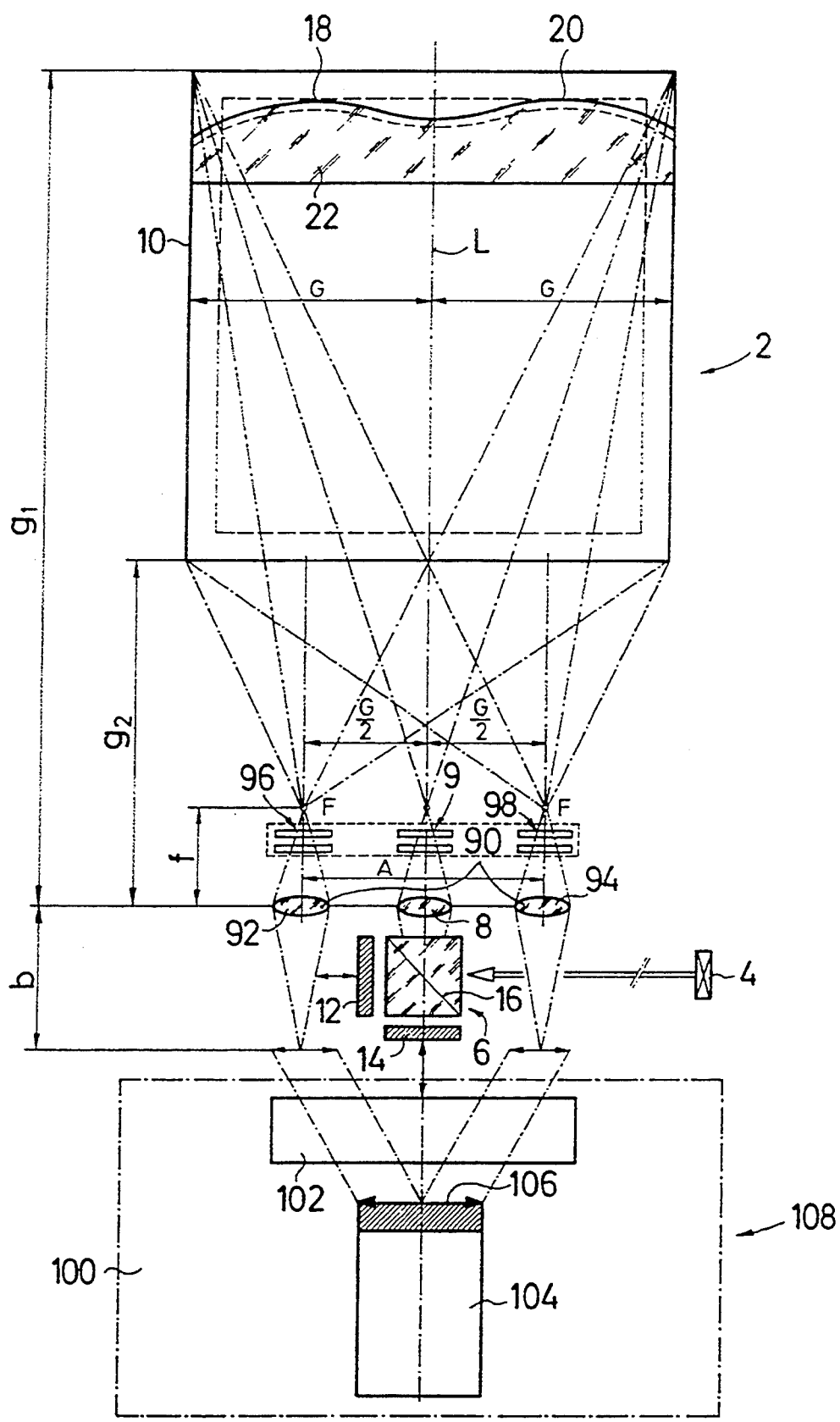
FIG. 1: a diagrammatic sketch showing the principles of a scanning device according to the present invention.

The scanning device 2 that is shown in FIG. 1 consists essentially of a projection device, a recording device, and an evaluation device, the projection device and the recording device being formed in part from the same elements in the present case. The projection device incorporates a source of optical radiation 4 that is in the form of a laser or a laser diode, for example. The light from this is projected onto the surfaces of the buccal cavity in the area of the upper and lower jaws by means of an interferometer 6, through an optical illuminating system 8 that can optionally incorporate an electronically controllable polarizer 9 and a deflection device 10 (in the form of a strip pattern). However, the light can also be projected directly onto the teeth, i.e., without passing through an interferometer 6, in order to determine the color of the teeth. In this case, a light source that radiates light that is similar to sunlight, or ultra-violet light, or tungsten light, is used as the light source. Color measurement itself is effected by means of an RGB sensor. The interferometer 6 is a Michelson interferometer that incorporates two adjustable mirrors 12, 14 and a semi-transparent parallel-sided plate 16. The mirrors 12, 14 can be adjusted piezo-electrically in order to provide for precise adjustment of the desired beam interval, or else can be adjusted to a prescribed and fixed interval. Of course, another type of interferometer can be used. The deflection device 10 incorporates a sinusoidal, aspherically shaped mirror 18 which is applied to a ground edge of a glass body 22, for example, by vaporization. The recording device similarly consists of the deflection device 10 and an optical recording system 90 that incorporates pair of stereoscopic lenses 92, 94 and optionally an electronically adjustable analyzer 96, 98 for polarized light. A digitizing device 100 of an evaluation device 108 is adjacent to the optical recording system 90 and includes a camera 104 with a line or plane sensor 106 and, optionally, folding optics 102. The signals from the digitizing device 100 are passed to a computer of the evaluation device (not shown herein) which, in turn, can incorporate a display for the visible representation of the reflection images that have been recorded.

FIG. 2 shows various views and cross sections of the measurement device that consists of the projection device, the recording device, and the digitizing device. The glass body 22 of the deflection device 10 that has the mirror 18 on its rear edge 20 which, in the drawing, is transparent above and below and which is essentially formed at the sides from a housing end piece 52 and two housing side pieces 54, 56. An outer housing 80, which accommodates a drive unit 82 for linear movement of the glass body 22 with the mirror 18 in the direction of a longitudinal axis L, in addition to the optical illuminating system 8 and the optical recording system 90, is adjacent to an (intra-oral) housing 50 that is meant to be introduced into the buccal cavity.

Figure 3A:
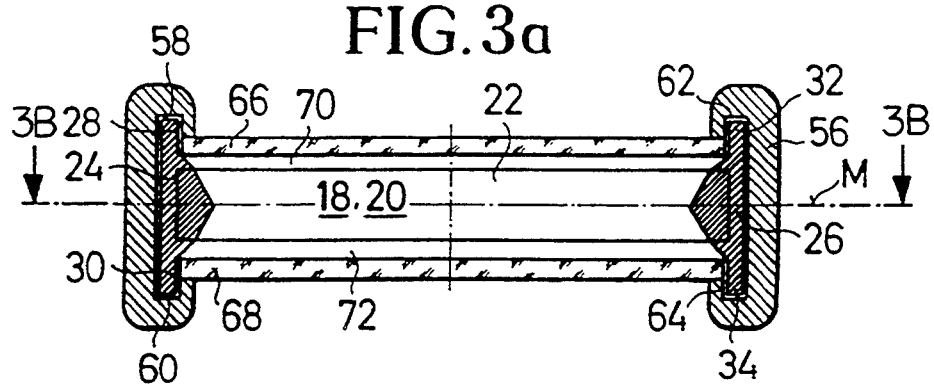
Figure 3B:
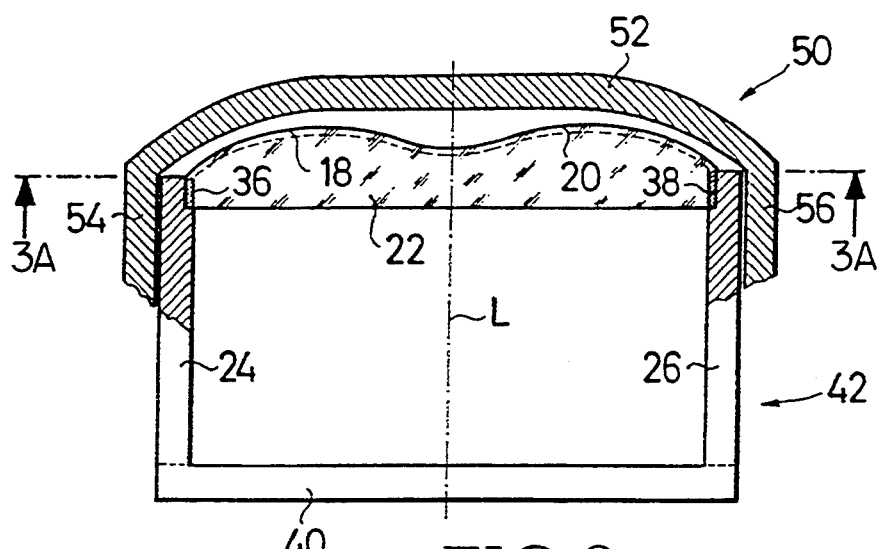
FIG. 3b.

FIGS. 3a and 3b provide a clearer representation of the construction of the intra-oral deflection device 10. Right-hand and left-hand supporting rails 24, 26, which are parallel, are secured to the glass body 22 that incorporates the mirror 18. In order to enhance rigidity these are provided with projections 28, 30, 32, 34 that are oriented upwards and downwards with reference to the horizontal center plane M. The projections 28, 30, 32, 34 of the supporting rails 24, 26 extend in grooves 58, 60, 62 and 64 of the housing side pieces 54, 56 of the housing 50. The supporting rails 24, 26 of the glass body 22 are not in contact with the housing 50, in order that external loads are not transferred to the sensitive deflection device 10. The glass body 22 is protected by an upper cover plate 66 and a lower cover plate 68, which can, at least in part, consist of transparent material. The cover plates 66, 68 can also be of polycarbonate or similar material or can at least incorporate an internal layer or an applied layer of such material. Between the glass body 22 and the cover plates 66, 68 there is an intermediate space 70, 72. The glass body 22 is installed in recesses 36, 38 in one side of the supporting rails 24, 26. On the other side of the supporting rails 24, 26 there is a cross piece 40 which, together with the supporting rails 24, 26 and the glass body 22, forms a mirror support 42. The projection device and the recording device are installed on the cross piece 40 of the mirror carrier 42 at a fixed interval from each other, which means that the depth of field is kept constant.

Figure 4A:
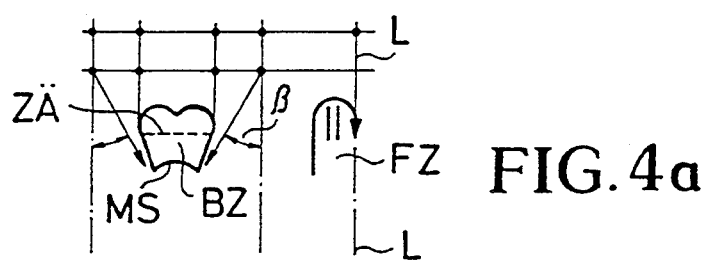
FIG. 4a: a rear view of the teeth with a diagrammatic representation of path of the beam, projected in a vertical plane, of the radiation reflected from the aspherical sinusoidal mirror.

FIG. 4a shows the different angles of reflection of the light beams from the projection device that strike the mirror that is arranged on the edge 20 of the glass body 22. The sinusoidal configuration of the mirror 18 ensures even and panoramic illumination of both incisors FZ as well as of molars BZ, and the marginal space MS or the crown edge that projects within the tooth equator ZÄ. FIG. 4a shows the path of the beams in a vertical plane, whereas FIG. 4b shows the path of the beams in the horizontal plane.

FIGS. 5a and 5b show the position of the glass body 22 of the deflection device 10 relative to the teeth that are to be measured. The quadrilateral that is formed by the dashed lines in FIG. 5a show the position of the rearmost molars BZ, which are the so-called seventh or eighth molars. The glass body 22 is then in its rearmost position, so that the rear surfaces of the seventh or eighth molars can still be covered. In FIG. 5b, the glass body 22 that is inserted between the upper and the lower dentition is shown in vertical cross section. The cover plates 66, 68, on which the teeth can bite in order to fix their position or to measure the forces involved are only shown in the area of the bite-down zone of the teeth in the upper and lower jaws.

Figure 4B:
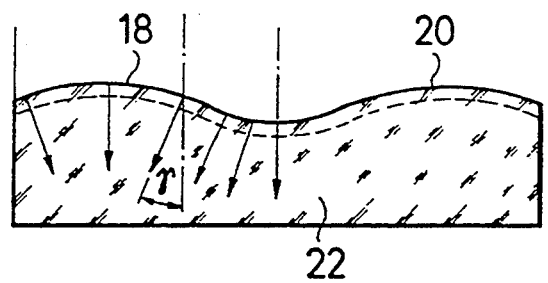
FIG. 4b: a diagrammatic representation in plan view of the path of a beam of radiation that is reflected from a glass body provided with an aspherical sinusoidal mirror.

FIG. 6a shows the face-side profile of the glass body 22 on its reflection edge 20 that is provided with the mirror 18, which ensures that the projection beams are deflected both upwards and downwards, whereas the mirror curvature that is shown in FIGS. 4b and 5a causes lateral deflection. The light beams R which are thrown from the projection device parallel onto the mirror 18 that is on the front edge 20 of the glass body 22 are reflected equally upwards and downwards because of the parabolic shape of the mirror, so that the whole of the buccal cavity can be illuminated simultaneously. In contrast to this, because of the special configuration of the mirror, the reflection beams that are returned by the surfaces of the buccal cavity that are to be measured are deflected in a direction parallel to the longitudinal axis L.

The shape of the edge 20 of the glass body 22, which is provided with a mirror 18, as is shown in FIG. 6b, also deflects the light beams R that are radiated by the projection device into the upper and lower buccal cavity, when each of the deflection angles is constant. Such a V-shaped mirror can be manufactured easily and is suitable for line-by-line scanning of the buccal cavity. FIG. 6c shows a glass body 22 with a W-shaped contour of the edge 20, in which only the outer sections are provided with the mirror 18, whereas the two inner sections have unmirrored surfaces 19. The light beams R that are radiated from the projection device are not reflected in these sectors but are broken on the boundary surfaces because of the different density of the glass body 22 and the surrounding air. The angle of deflection on the unmirrored surfaces 19 of the glass body 22 is comparatively small, so that even the surfaces of the buccal cavity that are behind the glass body 22 can be illuminated.

FIG. 6d shows a similarly W-shaped contour of the edge 20, in which the unmirrored surfaces 19 of the glass body 22 are arranged on the outside and the mirror 18 is arranged on the inside. The edge 20 of the glass body 22 can have a semi-circular, a facet-like or other suitable shape in the horizontal and in the vertical direction. Furthermore, deflection by way of holographic elements can also be achieved.

Figure 7:
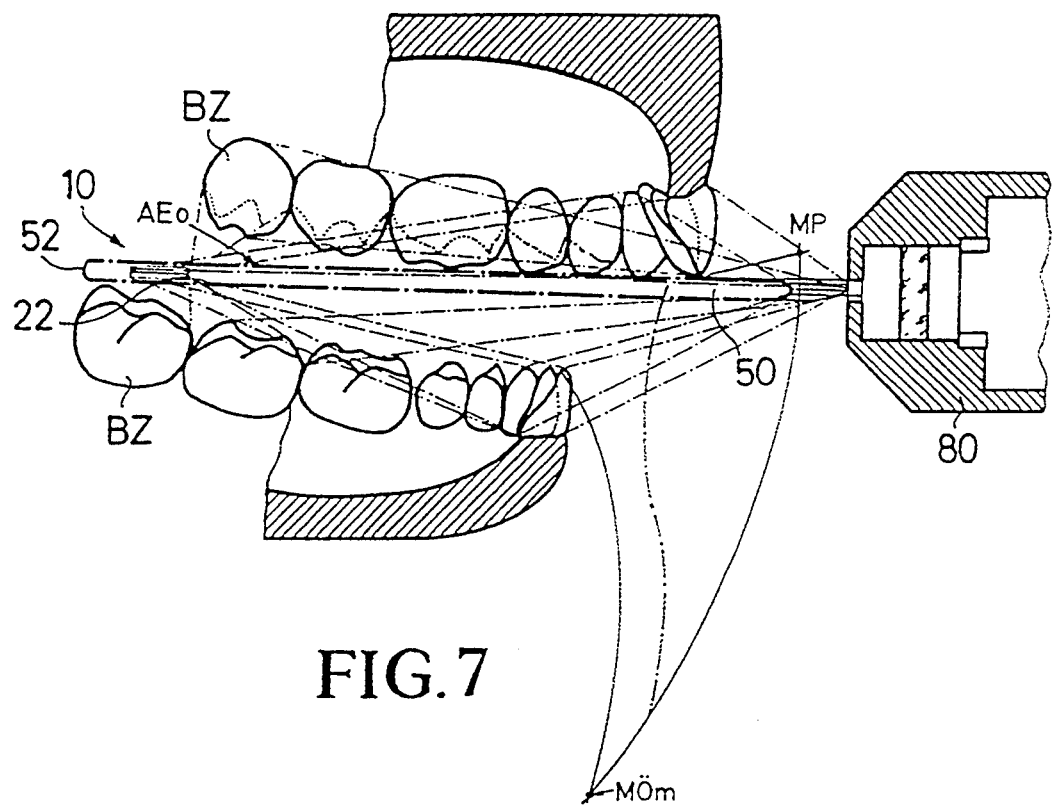
FIG. 7: a diagrammatic representation in side view of a section of the measurement device according to the present invention when inserted between the upper and lower jaw.

FIG. 7 is a diagrammatic view of the measurement system when the front intra-oral section of the device is inserted into the buccal cavity. The deflection device 10 then lies with its housing 50 on the lower side of the teeth of the upper jaw. The mirrored glass body 22 of the deflection device 10 is also shown in both its maximally extended position in which it projects the radiation from the optical illuminating system 8 onto the backs of the teeth as well, or else deflects the reflected radiation from the back of the teeth to the optical recording system 90, as well as in its maximally retracted position, in which it moves almost completely into the outer housing 80 and illuminates the fronts of the incisors or else deflects the reflections from them to the optical recording system 90. By triggering the radiation, it is possible to generate high contrast images without any blurring due to movement (shutter effect). The lower jaw can be moved up and down during measurement in order to provide for exact determination of the movement function of the mandibular joint.

Figure 8A:
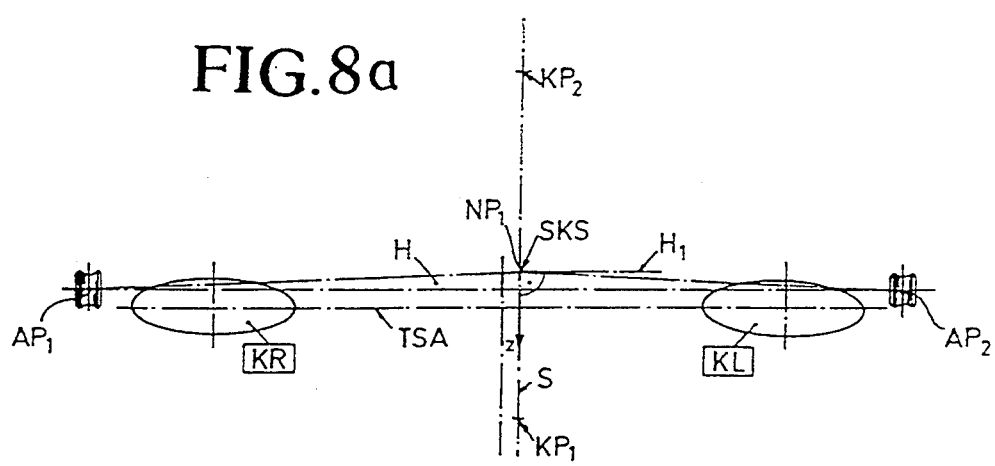
FIG. 8: a vertical cross section of a schematic representation of the position of the intra-oral section of the device relative to the teeth of the upper and lower jaw and to other defined points of the skull.
Figure 8B:
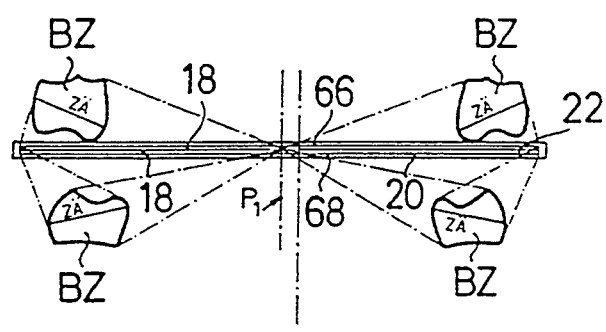

In FIG. 8, the position of the glass body 22 of the deflection device 10 is shown relative to the tooth equator ZÄ of the molars BZ. The replicable position of the glass body 22 relative to the different points of the skull is important for evaluating the measured data. To this end, three fixed points, e.g., the nasal point $NP_1$ and the eye points $AP_1$ and $AP_2$, are defined on the skull; these then define a co-ordinate space and permit replicable positioning of the scanning device 2. These defined fixed points are also taken into consideration during x-ray photography of the skull so that a precise co-ordinate coincidence of the optical images and the x-ray images can be produced.

Figure 9:
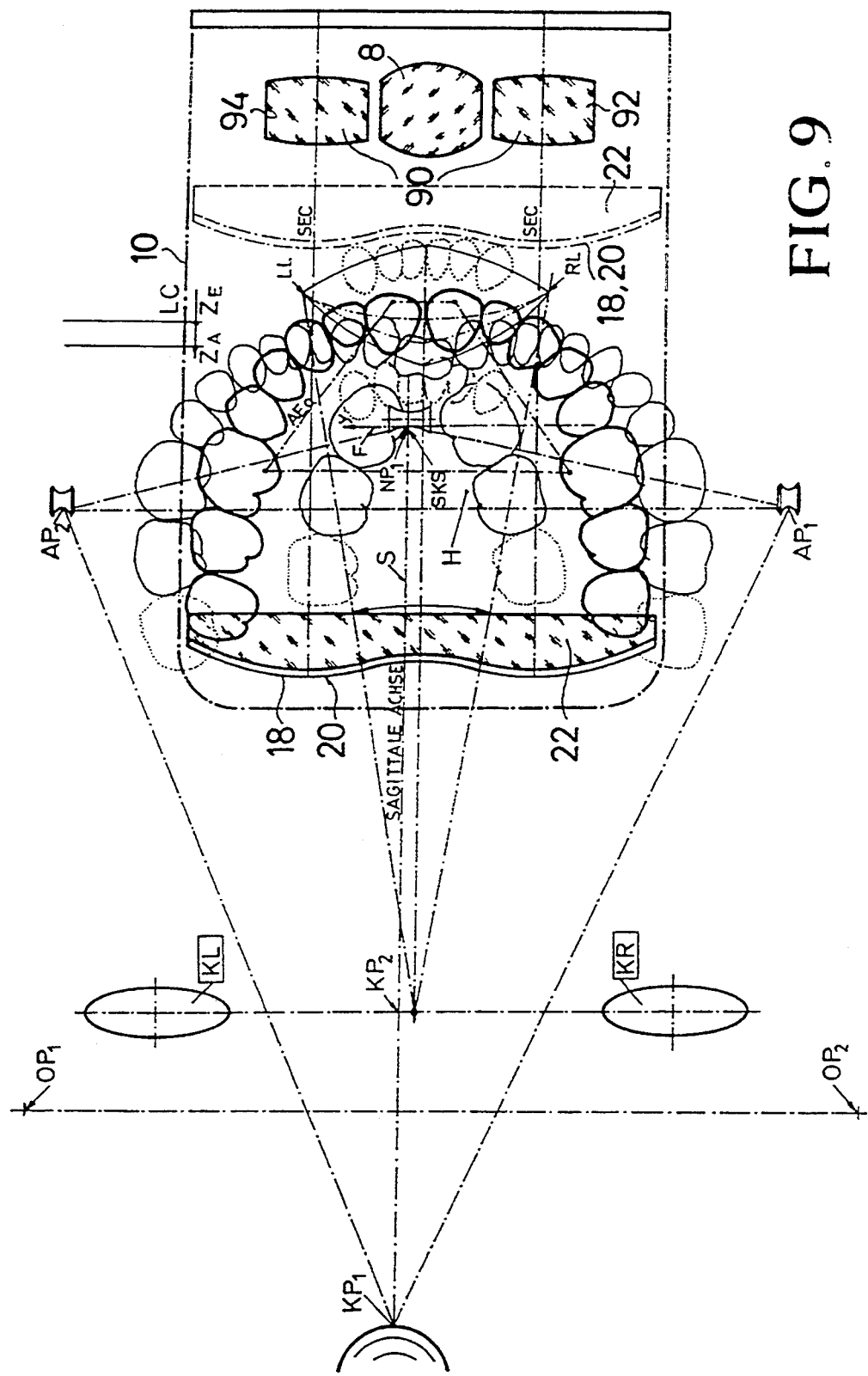
FIG. 9: a plan view of a schematic representation of the different positions of the intra-oral section of the scanning device according to the present invention relative to the defined points of the skull.

FIG. 9 shows the geometric position of the optical illuminating system 8 and the optical recording system 90 relative to the deflection device 10 and the position of the glass body 22 of the deflection device 10 that is provided with the mirror 18 relative to the defined points on the skull and to the dentition of the lower or upper jaw that is to be recorded, even if the intra-oral section of the device shifts sideways relative to the latter. In order to be able to map the images obtained with the scanning device 2 and those obtained by x-ray technology, three lead balls, for example, can be attached at the fixed points of the skull; these then define a co-ordinate system for measurement with the scanning device 2, and can also be precisely identified by means of x-ray technology, so that the optical images obtained by the scanning device 2 can be mapped precisely to the x-ray images with reference to the co-ordinate system on the skull.

In order to measure the upper and lower dentition, the intra-oral housing 50 is first inserted between the upper and lower dentition so that the teeth of the upper and the lower dentition lie in part on the upper or lower cover 66 or 68, respectively, of the housing 50 of the deflection device 10. When the intra-oral section of the apparatus has been correctly inserted, the laser or laser diode of the projection device, which is provided as a source of optical radiation 4, is switched on. In order to provide simultaneous geometric-topographic measurement of the upper and lower dentition, the light from the laser or laser diode is passed directly to the interferometer 6, either directly or through a photoconductor 15 and from there projected through the optical illuminating system 8 and optionally through a polarizer 9 in the direction of the longitudinal axis L of the scanning device 2 and onto the mirror 18 of the deflection device 10 in the form of a strip pattern. From there, the strip pattern that is generated by means of interference is deflected into the buccal cavity of the upper and lower jaw area, and the radiation that falls onto the upper half of the glass body 22 relative to the middle plane M is deflerted into the upper jaw area and the radiation which falls onto the lower half of the glass body 22 relative to the horizontal middle plane M is deflected into the lower jaw area. The mirror 18 or the glass body 22, respectively, can be parabolic, a V- or W-shape, semi-circular, or any other suitable profile. Depending on the profile and the position of the mirror 18 or of the glass body 22, respectively, the strip pattern that is generated by the interferometer 6 is correspondingly projected, distorted, onto the surface and/or the translucent interior volume of the buccal cavity, in particular of the translucent teeth, where it forms a fine pattern of light and dark strips.

The projected strip pattern is reflected from the surface and/or from the translucent internal volume of the buccal cavity, in particular from the translucent teeth, depending on the geometrictopographic configuration and/or from the transparent internal volume according to the three-dimensional arrangement of pigment and passes through the mirror 18 or the glass body 22 to the deflection device 10 of the optical recording system 90, and if necessary through photo or image conductors. The recording optical system forms the reflected strip pattern, optionally through the folding optics 102, on the line or plane sensor 106 or a video camera 104. The video camera 104 processes the optical signals that are received into electronic signals and stores these in a computer (not shown herein). There, the electronic signals can be so evaluated by means of complex computing processes, taking numerous parameters into consideration, such as the wavelength of the projected and the recorded light, the theoretical strip interval of the strip pattern, the position of the deflection mirror relative to the projection device, the shape of the deflection mirror, the shape of the glass body, the refractive index of the glass body, the thickness of the covers, the refractive index of the covers, the type of optical lenses in the illuminating and recording optical system, and the parallax interval between the pair of stereoscopic lenses. This is done such that the geometric-topographic formation of the buccal cavity and the arrangement of pigment in the three-dimensional translucent space, in particular within the interior volume of the teeth, can be determined very precisely. The surface topography of the buccal cavity and the arrangement of colour within the interiors of the translucent teeth can be shown three-dimensionally on a monitor.

Instead of optical radiation, which is particularly suitable, x-rays, radar, or ultrasonic methods can be used to measure the geometric-topographic configuration of the buccal cavity. The deflection elements of the deflection system must in each instance be adapted to the type of radiation that is used.

In order to measure the effective forces, the semitransparent and mirrored cover plates 66, 68 of the deflection device 10, which consist, for example, of polycarbonate or which are provided with inserted layers or applied layers of such material, are irradiated with polarized light from a source of optical radiation 4 from the projection device, light being polarized, for example, by means of a polarizer 9. Because of this, striated impressions are formed in the cover plate 66, 68, which, in the reflected light, can be used to determine the forces that are introduced into the cover plate 66 and 68 by means of an analyzer 96, 98 that is preferably arranged in the optical recording system 90, by means of isochromatic evaluation so that the scanning device can also be used for precise measurement of forces with reference to the position of the mandibular joint or (by extrapolation) with reference to tooth contact. Force measurements of this kind can also be accomplished in the manner known per se using pyro-electric detectors.

| | |
|---|---|
| A | PARALLAX INTERVAL |
| B | IMAGE SIZE |
| BZ | MOLAR |
| D | LENS DIAMETER |
| F | FOCAL POINT |
| FZ | INCISOR |
| G | SIZE OF OBJECT |
| L | LONGITUDINAL AXIS |
| M | CENTRE PLANE |
| MS | GUM LINE |
| R | REFLECTED RADIATION |
| S | DEPTH OF FIELD |
| T | OBJECT DEPTH |
| ZA | TOOTH EQUATOR |
| b | LENS MIDDLE-IMAGE PLANE INTERVAL |
| f | FOCAL LENGTH |
| g | LENS MIDDLE-OBJECT PLANE INTERVAL |
| $\alpha$ | ANGLE OF CURVATURE |
| $\beta$ | ANGLE OF REFLECTION (VERTICAL) |
| $\gamma$ | ANGLE OF REFLECTION (HORIZONTAL) |

I claim:

1. A process for measuring the dimensions of a buccal cavity having upper and lower dentition, comprising the steps of:

inserting an optical measurement device at least in part into a buccal cavity, the optical measurement device including an optical radiation projection device having a radiation source and a recording device;

simultaneously projecting optical radiation from the radiation source with the optical radiation projection device onto portions of both the upper and lower dentition of the buccal cavity by deflecting the optical radiation from the optical radiation projection device with a deflection device; and simultaneously transmitting radiation reflected from the portions of both the upper and lower dentition of the buccal cavity to the recording device with the deflection device;

wherein said step of simultaneously projecting comprises projecting the optical radiation in the form of an interference generated strip.

2. The process of claim 1, and further comprising the step of recording the reflected radiation with the recording device operating on a principle selected from the group consisting of the principle of stereophotogrammetry, the triangulation principle and the principle of a hologram.

3. The process of claim 2, wherein said step of simultaneously projecting comprises projecting the optical radiation onto the portions of both the upper and lower dentition of the buccal cavity as a result of relative movement of at least one of the projection device, the recording device and the deflection device relative to the buccal cavity.

4. The process of claim 3, and further comprising reproducing optical signals of the reflected radiation on a plane sensor.

5. The process of claim 4, wherein folding optics are used to reproduce the optical signals of the reflected radiation on the plane sensor.

6. The process of claim 2, and further comprising reproducing optical signals of the reflected radiation on a plane sensor.

7. The process of claim 6, wherein folding optics are used to reproduce the optical signals of the reflected radiation on the plane sensor.

8. A process for measuring the dimensions of a buccal cavity having upper and lower dentition, comprising the steps of:

inserting an optical measurement device at least in part into a buccal cavity, the optical measurement device including an optical radiation projection device having a radiation source and a recording device;

simultaneously projecting optical radiation from the radiation source with the optical radiation projection device onto portions of both the upper and lower dentition of the buccal cavity by deflecting the optical radiation from the optical radiation projection device with a deflection device;

simultaneously transmitting radiation reflected from the portions of both the upper and lower dentition of the buccal cavity to the recording device with the deflection device;

converting optical signals of the reflected radiation into electronic signals and evaluating the electronic signals with a computer; and processing the electronic signals with the computer so as to form images and displaying the images on a monitor.

9. The process of claim 8, wherein the electronic signals are processed by a CAD modelling system and transmitted to a CAM manufacturing system for the production of replacement parts for teeth.

10. A scanning device, comprising:

means for simultaneously projecting optical radiation onto portions of both upper and lower dentition of a buccal cavity;

a recording device comprising an optical recording system and means for simultaneously transmitting radiation reflected from the portions of both the upper and lower dentition of the buccal cavity to said optical recording system;

an evaluation device for evaluating reflected radiation from said recording device; and a deflection device that is a component of said means for simultaneously transmitting and said means for simultaneously projecting;

wherein said deflection device comprises a glass body having an edge that is at least one of the group consisting of mirrored, partially mirrored, semi-transparently mirrored, provided with facet like deflection elements and provided with holographic deflection elements.

11. The scanning device of claim 10, wherein said glass body is disposed on a carrier that is provided with supporting rails.

12. The scanning device of claim 12, and further comprising an extra-oral linear guide system connected with said carrier for movement of said carrier relative to the buccal cavity.

13. The scanning device of claim 12, wherein said means for simultaneously projecting comprises a projection device that includes an optical illuminating system, and said deflection device forming a component of said projection device, said optical illuminating system having a longitudinal axis and said carrier being moveable in the direction of said longitudinal axis.

14. The scanning device of claim 13, wherein said optical recording system of said recording device is adjustable relative to said carrier in at least one of the directions selected from the group consisting of perpendicularly to a horizontal middle plane of said glass body, horizontally in the plane of said horizontal middle plane, and perpendicularly to said longitudinal axis.

15. A scanning device, comprising:

means for simultaneously projecting optical radiation onto portions of both upper and lower dentition of a buccal cavity;

a recording device comprising an optical recording system and means for simultaneously transmitting radiation reflected from the portions of both the upper and lower dentition of the buccal cavity to said optical recording system;

an evaluation device for evaluating reflected radiation from said recording device; and a deflection device that is a component of said means for simultaneously transmitting and said means for simultaneously projecting;

wherein said deflection device is disposed in a housing that is at least partially transparent; and wherein said housing comprises a layer of polycarbonate material for the optical measurement of stresses.

16. A scanning device, comprising:

means for simultaneously projecting optical radiation onto portions of both upper and lower dentition of a buccal cavity;

a recording device comprising an optical recording system and means for simultaneously transmitting radiation reflected from the portions of both the upper and lower dentition of the buccal cavity to said optical recording system; and an evaluation device for evaluating reflected radiation from said recording device;

wherein said scanning device comprises an intra-oral section and an extra-oral section, and said intra-oral section comprises a force measurement device.

17. The scanning device of claim 16, wherein said force measurement device comprises a pyro-electric detector.

18. The scanning device of claim 17, wherein said pyro-electric detector comprises layers of pyro-electric material that are biaxially oriented.

19. The scanning device of claim 16, wherein said force measurement device comprises an optical isochromatic evaluation device.

20. A scanning device, comprising:
an optical radiation source;
an interferometer receiving optical radiation from said optical radiation source;
an optical illuminating system receiving optical radiation from said interferometer;
a deflection device deflecting optical radiation from said optical illuminating system and reflected optical radiation, said deflection device having a horizontal center plane dividing said deflection device such that optical radiation from said optical illuminating system on opposite sides of said horizontal center plane are deflected in opposite directions;
an optical recording system receiving reflected radiation from said deflection device; and
an evaluation device evaluating reflected radiation from said optical recording system.

21. The scanning device of claim 20, wherein said scanning device comprises an intra-oral section and an extra-oral section.

22. The scanning device of claim 21, wherein said source of optical radiation and said evaluation device are located in said extra-oral section.

23. The scanning device of claim 24, wherein said intra-oral section comprises a carrier supporting said deflection device and said extra-oral section comprises a linear guide system connected with said carrier for movement of said carrier relative to the buccal cavity.

24. The scanning device of claim 20, wherein said deflection device comprises a mirror system.

25. The scanning device of claim 20, wherein said deflection device comprises at least one selected from the group consisting of a multiple mirror, facet-like deflection elements and holographic deflective elements.

26. The scanning device of claim 20, wherein said deflection device comprises a glass body having an edge that is at least one of the group consisting of mirrored, partially mirrored, semi-transparently mirrored, provided with facet-like deflection elements and provided with holographic deflection elements.

27. The scanning device of claim 20, wherein said deflection device is disposed in a housing that is at least partially transparent.

28. The scanning device of claim 20, wherein said evaluation device comprises a digitizing device for digitizing optical signals of the reflected radiation.

29. The scanning device of claim 20, wherein said digitizing device comprises a video camera.

30. The scanning device of claim 29, wherein said digitizing device further comprises a plane sensor and a system of folding optics for converting the reflected radiation from a line pattern into an area pattern.

* * * * *